(12) United States Patent
Miyano et al.

(10) Patent No.: US 10,907,155 B2
(45) Date of Patent: Feb. 2, 2021

(54) PHARMACEUTICAL COMPOSITION FOR TREATING AND/OR PREVENTING CANCER

(71) Applicant: TORAY INDUSTRIES, INC., Tokyo (JP)

(72) Inventors: Atsuko Miyano, Kamakura (JP); Aiko Takayama, Kamakura (JP); Hiroko Sudo, Kamakura (JP); Taiga Arai, Kamakura (JP)

(73) Assignee: TORAY INDUSTRIES, INC., Tokyo (JP)

( * ) Notice: Subject to any disclaimer, the term of this patent is extended or adjusted under 35 U.S.C. 154(b) by 0 days.

(21) Appl. No.: 16/321,260

(22) PCT Filed: Aug. 9, 2017

(86) PCT No.: PCT/JP2017/028866
§ 371 (c)(1),
(2) Date: Jan. 28, 2019

(87) PCT Pub. No.: WO2018/030450
PCT Pub. Date: Feb. 15, 2018

(65) Prior Publication Data
US 2019/0169617 A1    Jun. 6, 2019

(30) Foreign Application Priority Data
Aug. 9, 2016    (JP) .................. 2016-156375

(51) Int. Cl.
| | | |
|---|---|---|
| *A61K 48/00* | (2006.01) | |
| *C07H 21/04* | (2006.01) | |
| *C12N 15/113* | (2010.01) | |
| *A61K 31/7105* | (2006.01) | |
| *A61K 31/711* | (2006.01) | |
| *A61P 35/00* | (2006.01) | |

(52) U.S. Cl.
CPC .......... *C12N 15/113* (2013.01); *A61K 31/711* (2013.01); *A61K 31/7105* (2013.01); *A61K 48/00* (2013.01); *A61K 48/0058* (2013.01); *A61P 35/00* (2018.01)

(58) Field of Classification Search
CPC ............ C12N 15/113; C12N 2310/141; C12N 2320/30; A61K 31/713
See application file for complete search history.

(56) References Cited

U.S. PATENT DOCUMENTS

| | | | | |
|---|---|---|---|---|
| 2015/0057165 A1* | 2/2015 | Dave | .................. | C12Q 21/6886 435/6.12 |
| 2015/0133521 A1* | 5/2015 | Bloch | .................. | C12N 15/113 514/44 A |
| 2017/0275699 A1 | 9/2017 | Kawauchi et al. | | |

FOREIGN PATENT DOCUMENTS

| | | | | |
|---|---|---|---|---|
| WO | WO 2011/029903 A1 | 3/2011 | | |
| WO | WO 2011/057003 A2 * | 5/2011 | .......... | C12N 15/113 |
| WO | WO 2014/071205 A1 | 5/2014 | | |
| WO | WO 2015/153679 A1 | 10/2015 | | |
| WO | WO 2015/182781 A1 | 12/2015 | | |

OTHER PUBLICATIONS

Nakamura et al. (JCI Insight, Aug. 4, 2016, 1(12), e86820, pp. 1-17).*
Armstrong et al. (Molecular Cancer, 2015, 14:194, pp. 1-9).*
International Search Report, issued in PCT/JP2017/028866, PCT/ISA/210, dated Nov. 7, 2017.
Kojima et al. "MicroRNA Markers for the Diagnosis of Pancreatic and Biliary-Tract Cancers", PLOS One, 10(2), Feb. 23, 2015, p. 1-22.
Written Opinion of the International Searching Authority, issued in PCT/JP2017/028866, PCT/ISA/237, dated Nov. 7, 2017.

* cited by examiner

*Primary Examiner* — Amy H Bowman
(74) *Attorney, Agent, or Firm* — Birch, Stewart, Kolasch & Birch, LLP

(57) ABSTRACT

It is an object of the present invention to specify miRNA associated with the treatment and/or prevention of various cancer species, from among various miRNAs associated with cancer, and to provide a novel pharmaceutical composition for treating and/or preventing cancer which targets the specified miRNA. According to the present invention, provided are a pharmaceutical composition for treating and/or preventing cancer comprising, as an active ingredient, an antisense polynucleotide shown as hsa-miR4454, a combination drug comprising the aforementioned pharmaceutical composition and another antitumor agent, and a method for treating and/or preventing cancer, using the above-described pharmaceutical composition or combination drug.

8 Claims, 13 Drawing Sheets
Specification includes a Sequence Listing.

SEQUENCE LISTING

```
<160> NUMBER OF SEQ ID NOS: 6

<210> SEQ ID NO 1
<211> LENGTH: 20
<212> TYPE: RNA
<213> ORGANISM: Homo sapiens

<400> SEQUENCE: 1
ggauccgagu cacggcacca                                                     20

<210> SEQ ID NO 2
<211> LENGTH: 20
<212> TYPE: RNA
<213> ORGANISM: Homo sapiens

<400> SEQUENCE: 2
uggugccgug acucggaucc                                                     20

<210> SEQ ID NO 3
<211> LENGTH: 20
<212> TYPE: DNA
<213> ORGANISM: Homo sapiens

<400> SEQUENCE: 3
tggtgccgtg actcggatcc                                                     20

<210> SEQ ID NO 4
<211> LENGTH: 17
<212> TYPE: RNA
<213> ORGANISM: Homo sapiens

<400> SEQUENCE: 4
gggagucuac agcaggg                                                        17

<210> SEQ ID NO 5
<211> LENGTH: 20
<212> TYPE: RNA
<213> ORGANISM: Homo sapiens

<400> SEQUENCE: 5
ggggaggugu gcagggcugg                                                     20

<210> SEQ ID NO 6
<211> LENGTH: 22
<212> TYPE: RNA
<213> ORGANISM: Homo sapiens

<400> SEQUENCE: 6
acaggugagg uucuugggag cc                                                  22
```

PHARMACEUTICAL COMPOSITION FOR TREATING AND/OR PREVENTING CANCER

TECHNICAL FIELD

The present invention relates to a pharmaceutical composition for treating and/or preventing cancer comprising, as an active ingredient, the antisense polynucleotide of microRNA.

BACKGROUND ART

MicroRNA (miRNA) is a non-coding RNA having 16 to 28 nucleotides, and it is currently known that 2590 types of miRNAs are present in human according to miRBase release 21 (http://www.mirbase.org/). In recent years, miRNAs have been receiving attention as molecules for suppressing the expression of various genes in vivo. On a genome, a region for each of the miRNA genes is present, and a miRNA is transcribed as a RNA precursor in a hairpin loop by RNA polymerase II, cleaved by a dsRNA cleaving enzyme having 2 types of RNase III cleavage activities called Drosha in the nucleus and Dicer in the cytoplasm, thereby forming a mature miRNA. It is known that the mature miRNA is taken into a multiprotein complex called RISC and interacts with the mRNAs of a plurality of target genes having complementary sequences to thereby suppress the expression of a gene (Non Patent Literature 1).

Certain types of miRNAs are suggested to be related with human diseases including cancer. In particular, in cancer, for examples, many miRNAs such as hsa-miR-8073, hsa-miR-6893-5p and hsa-miR-4454 are known to be markers specific to pancreatic cancer in blood (Non Patent Literature 1 and Patent Literature 1).

Further, in addition to the miRNAs related to the growth of cancer cells, the presence of a miRNA which works in a direction of suppressing cancer cells is reported, suggesting a method for treating cancer utilizing the expression pattern of the miRNA. Specific examples of the known method include a method for treating diseases such as cancer by administering an activated serum comprising 153 miRNAs such as hsa-Let-7a to a subject, and upregulating the miRNA (Patent Literature 2), and a method for treating blood cancer by administering to a subject antisense oligonucleotides of many miRNAs such as miR-1321 comprised in circulating exosomes in the body (Patent Literature 3).

Moreover, there has been a report regarding a method for diagnosing and treating precursor lesions of pancreatic cancer, using 30 types of miRNAs such as hsa-Let-7a or hsa-miR4454 (Patent Literature 4). However, only the distinguishing between health conditions and precursor lesions of pancreatic cancer by the combination of the expression levels of individual miRNAs in the plasma could be experimentally confirmed in Patent Literature 4, and thus, the actual use of these miRNAs as a method for treating such precursor lesions of pancreatic cancer is hardly described in this publication.

CITATION LIST

Patent Literature

Patent Literature 1: International Publication No. WO 2015/182781
Patent Literature 2: International Publication No. WO 2011/029903
Patent Literature 3: International Publication No. WO 2014/071205
Patent Literature 4: International Publication No. WO 2015/153679

Non Patent Literature

Non Patent Literature 1: Kojima M PLoS One. 10(2) (2015) "MicroRNA markers for the diagnosis of pancreatic and biliary-tract cancer"

SUMMARY OF INVENTION

Technical Problem

It is an object of the present invention to specify miRNA associated with the treatment and/or prevention of various cancer species, from among various miRNAs associated with cancer, and to provide a novel pharmaceutical composition for treating and/or preventing cancer which targets the specified miRNA.

Solution to Problem

As a result of intensive studies directed towards achieving the aforementioned object, the present inventors have specified hsa-miR4454 to be miRNA associated with the growth of cancer cells from miRNAs, the expression of which is increased or decreased in the body fluids or tissues of cancer patients, and at the same time, the present inventors have found that the antisense polynucleotide of this miRNA is useful for the treatment and/or prevention of cancer, thereby completing the present invention.

Specifically, the present invention has the following features (1) to (11).

(1) A pharmaceutical composition for treating and/or preventing cancer comprising, as an active ingredient, the antisense polynucleotide of microRNA shown as hsa-miR4454.
(2) The pharmaceutical composition for treating and/or preventing cancer according to the above (1), wherein the antisense polynucleotide is RNA or DNA.
(3) The pharmaceutical composition for treating and/or preventing cancer according to the above (1) or (2), wherein the antisense polynucleotide comprises a nucleotide sequence having a sequence identity of 90% or more to a nucleotide sequence complementary to the nucleotide sequence as set forth in SEQ ID NO: 1.
(4) The pharmaceutical composition for treating and/or preventing cancer according to any one of the above (1) to (3), wherein the nucleotide sequence length of the antisense polynucleotide consists of 8 to 60 nucleotides.
(5) The pharmaceutical composition for treating and/or preventing cancer according to any one of the above (1) to (4), wherein the antisense polynucleotide consists of the nucleotide sequence as set forth in SEQ ID NO: 2 or 3.
(6) The pharmaceutical composition for treating and/or preventing cancer according to any one of the above (1) to (5), wherein the cancer expresses hsa-miR4454.
(7) The pharmaceutical composition for treating and/or preventing cancer according to any one of the above (1) to (6), wherein the cancer is colorectal cancer, breast cancer, lung cancer, liver cancer, pancreatic cancer, blood cancer, kidney cancer, brain tumors, stomach cancer, cervical cancer, ovarian cancer, prostate cancer, bladder cancer, esophagus cancer, fibrosarcomas, mast cell tumors, or melanomas.

(8) The pharmaceutical composition for treating and/or preventing cancer according to any one of the above (1) to (7), wherein the antisense polynucleotide is inserted into a vector, so that it can be expressed in the form of RNA or DNA.
(9) The pharmaceutical composition for treating and/or preventing cancer according to any one of the above (1) to (8), wherein the antisense polynucleotide is encapsulated into a carrier selected from the group consisting of non-cationic polymer carriers, liposome carriers, dendritic carriers, nano-material carriers, microparticle carriers, biostructural carriers, micelle carriers, polymer microparticles, and magnetic microparticles.
(10) A combination drug for treating and/or preventing cancer comprising, as active ingredients, the pharmaceutical composition for treating and/or preventing cancer according to any one of the above (1) to (9), and an antitumor agent.
(11) A method for treating and/or preventing cancer in a subject who suffers or has suffered from the cancer, comprising administering the pharmaceutical composition according to any one of the above (1) to (9), or the combination drug according to the above (10), to the subject.

Advantageous Effects of Invention

Since the pharmaceutical composition for treating and/or preventing cancer of the present invention effectively suppresses the growth of cancer cells, it is useful for treating or preventing cancer.

The present description includes the contents as disclosed in Japanese Patent Application No. 2016-156375, filed on Aug. 9, 2016, which is a priority document of the present application.

DESCRIPTION OF EMBODIMENTS

<Antisense Polynucleotide Serving as Active Ingredient>

Figure 1:
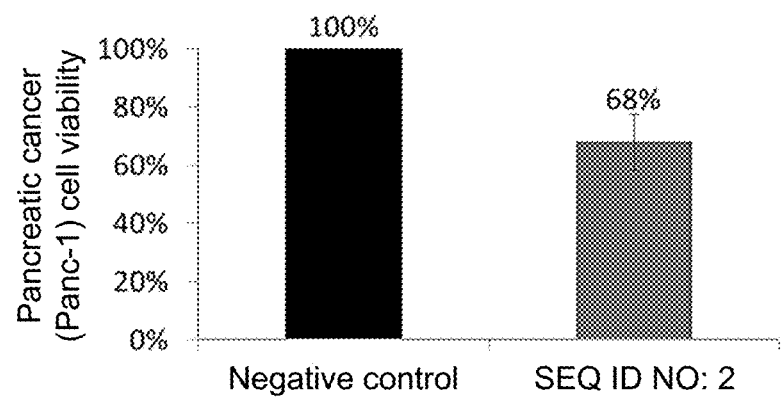
FIG. 1 shows the ratio (cell viability) of the viable cell count of the pancreatic cancer cell line Panc-1, into which the antisense RNA (SEQ ID NO: 2) of hsa-miR4454 as set forth in SEQ ID NO: 1 has been introduced, to the viable cell count (100%) of the pancreatic cancer cell line Panc-1, into which the synthetic RNA of a negative control oligo has been introduced.

The pharmaceutical composition for treating and/or preventing cancer of the present invention is characterized in that it comprises, as an active ingredient, the antisense polynucleotide of microRNA (hereinafter referred to as "miRNA") shown as hsa-miR4454 (SEQ ID NO: 1). Hereafter, the antisense polynucleotide that serves as an active ingredient in the present invention will be described.

It had been known that the miRNA shown as hsa-miR4454 (miRBase Accession No. MIMAT0018976) is a nucleotide sequence identified as human miRNA and is a part of miRNA serving as a marker specific to pancreatic cancer (Kojima M PLoS One. 10(2) (2015) "MicroRNA markers for the diagnosis of pancreatic and biliary-tract cancers."). The present inventors have newly found that this antisense polynucleotide suppresses the growth of pancreatic cancer and other cancer cells.

Accordingly, the antisense polynucleotide of the present invention is not particularly limited, as long as it comprises a nucleotide sequence having a sequence identity of 90% or more, preferably 95% or more, more preferably 98% or more, further preferably 99% or more, or 99.5% or more, to a nucleotide sequence complementary to hsa-miR4454 as set forth in SEQ ID NO: 1. That is to say, the antisense polynucleotide of the present invention may be either a polynucleotide specifically binding to hsa-miR4454, or a polynucleotide specifically binding to a nucleotide sequence to which hsa-miR4454 binds. The present antisense polynucleotide is preferably a polynucleotide specifically binding to hsa-miR4454.

The polynucleotide specifically binding to hsa-miR4454 as set forth in SEQ ID NO: 1 is a polynucleotide comprising a nucleotide sequence having an identity of at least 90% or more, preferably 95% or more, more preferably 98% or more, further preferably 99% or more, or 99.5% or more, to the nucleotide sequence as set forth in, preferably, SEQ ID NO: 2 or SEQ ID NO: 3. The present polynucleotide is still further preferably a polynucleotide comprising the nucleotide sequence as set forth in SEQ ID NO: 2 or SEQ ID NO: 3.

The nucleotide sequence as set forth in SEQ ID NO: 1, 2 or 3 is as shown in Table 1.

TABLE 1

| SEQ ID NO. | Nucleotide sequence | Gene name miRBase Accession No. |
|---|---|---|
| 1 | GGAUCCGAGUCACGGCACCA | hsa-miR-4454 (MIMAT0018976) |
| 2 | UGGUGCCGUGACUCGGAUCC | — |
| 3 | TGGTGCCGTGACTCGGATCC | — |

With regard to the antisense polynucleotide having the nucleotide sequence as set forth in SEQ ID NO: 2 or the antisense polynucleotide having the nucleotide sequence as set forth in SEQ ID NO: 3, it has not been reported so far that a compound comprising the sequence of the gene or the transcript thereof can suppress tumor cells.

The antisense polynucleotide of the present invention may have any structure, as long as it can exhibit the effect of treating and/or preventing cancer. The present antisense polynucleotide may have, for example, a single strand, a double strand, or a multiple structure consisting of three or more strands. The structure of the present antisense polynucleotide preferably has a single-stranded structure or a double-stranded structure, and more preferably a single-stranded structure.

The antisense polynucleotide of the present invention may be RNA, DNA, or RNA/DNA (chimera), as long as it can exhibit the effect of treating and/or preventing cancer. Besides, with regard to the antisense polynucleotide of the present invention, when the entire or a part of the nucleotide sequence corresponding to a sequence number shown in the sequence listing corresponds to DNA, U (uracil) in the region corresponding to the DNA in the nucleotide sequence shown in the sequence listing is replaced with T (thymine).

The form of DNA is, for example, cDNA. In addition, the form of RNA includes naturally-occurring RNA and synthetic RNA.

The antisense polynucleotide usable in the present invention may comprise at least one modified nucleotide analog. The modified nucleotide analog can be arranged, for example, at the 5' terminus, 3' terminus, and/or inside of an RNA molecule. In particular, by incorporation of such a modified nucleotide analog, the antisense polynucleotide can be further stabilized.

The modified nucleotide analog is preferably a sugar- or backbone-modified ribonucleotide, and more preferably a ribonucleotide having a modified nucleic acid nucleotide, and more specifically, a ribonucleotide comprising a non-naturally occurring nucleic acid nucleotide. Examples of the non-naturally occurring nucleic acid nucleotide include uridine modified at position 5, or cytidine, such as 5-methyluridine, 5-(2-amino)propyluridine, 5-methyl-2-thiouridine, 5-bromouridine, or 6-azouridine, adenosine and guanosine modified at position 8, such as 8-bromoguanosine, deazanucleotide, or 7-deaza-adenosine; and O- and N-alkylated nucleotides, N6-methyladenosine, and universal nucleotides.

Examples of a preferred sugar-modified ribonucleotide may include a ribonucleotide having a 2'-OH group of a sugar moiety that is substituted with a group selected from the group consisting of H, OR, halo, SH, SR, $NH_2$, NHR, $NR_2$ and CN, and a ribonucleotide comprising a 2'-O, 4'-C methylene bridge or an ethylene bridge (for example, LNA and ENA). Herein, R is C1 to C6 alkyl, alkenyl or alkynyl, and halo is F, Cl, Br or I. Further, the modified sugar moiety in such a sugar modified ribonucleotide may be mannose, arabinose, glucopyranose, galactopyranose, 4'-thioribose or other sugars, a hetero ring or a carbon ring.

Examples of a preferred backbone-modified ribonucleotide include ribonucleotides having a phosphoester group binding to a ribonucleotide adjacent thereto, which is substituted with, for example, a modifying group of a phosphothioate group, boranophosphate, 3'-(or 5')deoxy-3'-(or 5')aminophosphoramidate, hydrogen phosphonate, boranophosphate ester, phosphoramidate, alkyl, or aryl phosphonate and phosphotriester. Moreover, two or more types of the above-described modifications may be combined with one another.

<Carrier Added to Antisense Polynucleotide as Active Ingredient>

The pharmaceutical composition for treating and/or preventing cancer of the present invention may comprise a pharmaceutically acceptable carrier, in addition to the antisense polynucleotide of the present invention. The pharmaceutically acceptable carrier is preferably a substance, which facilitates the transport of the antisense polynucleotide of the present invention to a target cell or tissue, does not stimulate a living organism, and does not inhibit the activities and properties of the antisense polynucleotide of the present invention, and it is also preferable that the carrier itself does not induce the production of a harmful antibody to an individual, to which the composition is administered. The size of such a carrier is preferably a size which does not permeate normal blood vessel walls but can permeate newborn blood vessels in cancer tissues. When a carrier is an approximate spheroid, the diameter of the carrier may be preferably, for example, a nano size of about 1 nm or more and less than 100 nm.

The carrier may encapsulate the antisense polynucleotide of the present invention, or may movably bind to the antisense polynucleotide of the present invention. The phase "to movably bind to" refers to the electronic interaction between the carrier and one or more agents. The interaction is not limited, and may be in the form of any given chemical bonds, including a covalent bond, a polar covalent bond, an ionic bond, an electrostatic bond, a coordinate covalent bond, an aromatic bond, a hydrogen bond, and dipole or Van der Waals interaction.

The binding site of the antisense polynucleotide of the present invention and the carrier is preferably on the 5' terminal side or on the 3' terminal side, and more preferably on the 5' terminal side.

Specific examples of the carrier of the present invention include non-cationic polymer carriers, liposome carriers, dendrimer carriers, nano-material carriers, microparticle carriers, biostructural carriers, micelle carriers, polymer microparticles, and magnetic microparticles.

The non-cationic polymer carrier indicates, for example, an anionic (i.e., negatively charged) polymer, or an electronically neutral linear or branched polymer, which can encapsulate one or two or more agents therein, and/or can movably bind to such agent(s). The carrier may have the form of a microparticle or a nanoparticle, and may also be water-soluble or water-insoluble, or biodegradable or non-biodegradable carrier. Preferred non-cationic polymer carriers are known to those skilled in the art. The non-cationic polymer carrier may comprise, for example, poly-L-glutamic acid (PGA), poly-(γ-L-glutamyl glutamine) (PGGA), poly-(γ-L-aspartyl glutamine) (PGAA) or poly-(lactide-co-glycolide) (PLGA), and may also comprise a mixture of at least two polymers.

The liposome carrier indicates a lipid double layer structure comprising a lipid attached to a polar hydrophilic group, which forms a substantially closed structure, in which the liposome carrier can encapsulate one or two or more agents therein in an aqueous medium, and/or can movably bind to the agent(s). The liposome carrier may comprise a single lipid double layer (i.e., unilamellar) or may also comprise a concentric lipid double layer consisting of two or three or more layers (i.e., multilamellar). The liposome carrier may have an approximate spherical or approximate elliptical shape. Preferred liposome carriers are known to those skilled in the art, and can be selected based on various properties such as the rigidity of the lipid double layer, the electronic charge of the lipid double layer and/or the compatibility of one or both of the agents with the liposome carrier. Examples of the liposome carrier include natural phospholipids such as egg phosphatidylcholine, egg phosphatidylethanolamine, soy phosphatidylcholine, lecithin and sphingomyelin, synthetic phosphatidylcholine, lysophosphatidylcholine, phosphatidylglycerol, phosphatidic acid, phosphatidyl ethanolamine, dioctadecylamide glycylspermine, dioleoylphosphatidylethanolamine, N-1-2, 3-dioleyloxypropyl-N,N,N-trimethylammonium chloride, 2,3-diolexyoloxy-N-2-sperminecarboxamidoethyl-N,N-dimethyl-1-propaneammonium trifluoroacetamide, phosphatidylserine, derivatives thereof, and PEGylated lipids.

The dendritic carrier indicates a dendrimer, a dendron, or derivatives thereof, which can encapsulate and/or can movably bind one or two or more agents. The dendrimer indicates a giant molecule having a core and a plurality of branch-structured shells spreading from the core. The dendron is a type of dendrimer having branches spreading from a focal point. The dendritic carriers are commercially available or can be synthesized by a method known to those skilled in the art. At least a part of the dendritic carrier may be hydrophobic or hydrophilic. The dendritic carrier may be cationic, or electronically neutral or anionic. The dendritic carrier may comprise a core molecule, and examples of the dendritic carrier include alkyl diamines such as ethylenediamine, 1,4-diaminobutane, 1,6-diaminohexane and 1,12-diaminodecane; amines such as ammonia; alkylimines such as cystamine and polyethyleneimine (PEI); and chlorinated phosphorus molecules such as cyclotriphosphazene and thiophosphoryl. Additionally, the dendritic carrier may comprise alkylimines such as polypropyleneimine (PPI), tertiary amines such as polyamideamine (PAMAM), polyamino acids such as polylysine, and/or phenoxymethyl (methylhydrazono) (PMMH).

The nano-material carrier indicates a material having the longest dimension ranging from about 1 nm to about 100 nm, which can encapsulate one or two or more agents and/or can movably bind to the agent(s). Preferred nano-material carriers are known to those skilled in the art, and examples of the nano-material carrier may include a nanoparticle, nanopowder, nanocluster, nanocrystal, nanosphere, nanofiber, nanotube, nanogel, and/or nanorod. Additionally, examples of the substance constituting the nano-material carrier include poly-(lactide-co-glycolide) (PLGA), polyalkylcyanoacrylate (PACA), polyepsilon-caprolactone (PCL), polylactic acid (PLA), polyethyleneglycol (PEG), poly-N-vinylcaprolactam sodium acrylate, poly-N-isopropylacrylamide, and polyvinyl acetate. Further, in some aspects, the nano-material carrier may be fullerene, and the fulleren may include spherical fullerenes (e.g., C60), carbon nanotubes, and fullerene derivatives.

The microparticle carrier indicates a particle having the longest dimension ranging from about 100 nm to about 1000 μm. The microparticle may have various shapes and various forms. Examples of the substance constituting the microparticle carrier include poly-(lactide-co-glycolide) (PLGA), polyalkylcyanoacrylate (PACA), polyepsilon-caprolactone (PCL), polylactic acid (PLA), PLGA, and polyethyleneglycol (PEG).

The biostructural carrier indicates a polymer or a compound, in which a large number of units in the biostructural carrier are amino acids and/or saccharides, and which can encapsulate one or two or more agents therein and/or movably bind to the agent(s). Preferred biostructural carriers are known to those skilled in the art, and examples of the biostructural carrier may include any of sugars, monosaccharides, oligosaccharides, polysaccharides, cyclic polysaccharides, non-cyclic polysaccharides, linear polysaccharides, branched polysaccharides, amino acids, proteins, peptides, and semisynthesized derivatives thereof. Specific examples of the biostructural carrier may include any of α-cyclodextrin, β-cyclodextrin, γ-cyclodextrin, methyl β-cyclodextrin, dimethyl-β-cyclodextrin, carboxymethyl-β-cyclodextrin, hydroxypropyl-β-cyclodextrin, sulfobutyl ether-β-cyclodextrin, tri-O-methyl-β-cyclodextrin, glucosyl-β-cyclodextrin, β1,3D glucan, β1,6 glucan, C-reactive protein, conalbumin, lactalbumin, ovalbumin, parvalbumin, serum albumin, technetium TC99m aggregated albumin, human serum albumin (HSA), bovine serum albumin (BSA), recombinant human serum albumin (rHSA), glucose (dextrose), fructose, galactose, xylose, ribose, sucrose, cellulose, cyclodextrin, and starch.

The micelle carrier is a lipid, any fat-soluble (i.e., lipophilic) molecule, oil, wax, sterol, monoglyceride, diglyceride, triglyceride, phospholipid, etc., which has the form of a micelle structure. Examples of the micelle carrier may include any of polyalkylene glycols such as polyethylene glycol (PEG); polyamino acids such as polyaspartic acid and polyglutamic acid (PGA); poly-(γ-L-glutamyl glutamine) (PGGA), polyphenyleneoxide (PPO), poly(ε-caprolactone) (PCL), poly-(lactide-co-glycolide) (PLGA), and a diblock copolymer.

Further, the carrier may also be a conjugate. Examples of such a conjugate may include a nucleotide linker, a non-nucleotide linker or a nucleotide/non-nucleotide complex linker, which connects a sense region and an antisense region of a nucleic acid, polyethylene glycol, human serum albumin, and a ligand to a cell receptor, capable of inducing the cellular uptake. Additionally, the nucleotide linker may be a linker having 2 or more nucleotides in length, or may also be a nucleic acid aptamer.

The pharmaceutical composition for treating and/or preventing cancer comprising the antisense polynucleotide of the present invention may further comprise at least one selected from pharmaceutically acceptable excipients, pharmaceutical carriers and diluents. By further adding a diluent, a dispersant, a surfactant, a binder, a lubricant and/or a mixture thereof to the antisense polynucleotide of the present invention, the present antisense polynucleotide can be formulated into any given dosage forms including parenteral dosage forms such as injection dosage forms, or forms suitable for intrarectal, intranasal, local, subcutaneous, vaginal or other parenteral administration, or oral dosage forms such as pills, capsules, granules or tablets, or forms suitable for inhalation or infusion administration.

When the antisense polynucleotide of the present invention is used as a liquid preparation, the carrier is preferably a sterilized carrier that is suitable for a living body, and further, other common additives such as an antioxidant, a buffer solution and a bacteriostatic agent may also be added to the carrier. Examples of preferred additives include, but are not limited to, giant molecules that are slowly metabolized, such as proteins, polysaccharides, polylactoses, polyglycolic acids, polymeric amino acids, amino acid copolymers, lipid aggregates, hydrogels, inactivated virus particles, and collagens. Further, a liquid preparation comprising the antisense polynucleotide of the present invention may comprise liquids such as water, a saline, sterilized water, a Ringer's solution, a buffered saline, an albumin injection solution, a dextrose solution, a maltodextrin solution, glycerol or ethanol, and may also comprise adjuvants such as a wetting agent, an emulsifier, or a pH buffering substance.

In the present invention, the term "administration" means introduction of the antisense polynucleotide of the present invention, or a pharmaceutical composition for treating and/or preventing cancer comprising, as an active ingredient, the antisense polynucleotide of the present invention, into a subject by any suitable method. Examples of such administration include the delivery of the antisense polynucleotide of the present invention by a viral or non-viral technique, and transplantation of cells which express the antisense polynucleotide of the present invention.

The administration can be carried out via various oral or parenteral administration routes, as long as the composition can reach a target tissue. For example, the administration can be carried out by an intraoral, intrarectal, local, intravenous, intraperitoneal, intramuscular, intraarterial, transdermal, intranasal, inhalation, intraocular, or intradermal route.

The applied dose is different depending on the purpose of administration, an administration method, the type and size of a tumor, conditions (sex, age, body weight, etc.) of a target person to be administered (i.e., a subject). Typically, with regard to drug dose, a drug is administered at a lower level and is then increased until the intended effect is achieved. A preferred dose of the antisense polynucleotide of the present invention may range, for example, from 1 pmol to 100 nmol per kg of body weight, and it may also range from 0.001 to 0.25 mg per kg of body weight, or from 0.01 to 20 µg per kg of body weight, or from 0.10 to 5 µg per kg of body weight, but not limited thereto. The above doses are desirably administered preferably 1 to 10 times, and more preferably 5 to 10 times.

<Suppression of Cancer by Antisense Polynucleotide>

The antisense polynucleotide of the present invention may be provided in the form of an antisense polynucleotide introduced into a cell. The phrase "introduced into a cell" means the inflow of an exogenous antisense polynucleotide into a cell by transfection or transduction. The transfection means, for example, calcium phosphate-DNA co-precipitation method, DEAE-dextran-mediated transfection method, polybrene-mediated transfection method, electroporation method, microinjection method, liposome fusion method, Lipofectamine transfection, and protoplast fusion method. On the other hand, the transduction means the transfer of a gene into other cells by means of infection using a virus or a virus vector particle (e.g., adenovirus, adeno-associated virus, Sendai virus, or retrovirus (lentivirus, etc.)) or using a plasmid vector. The vector can comprise necessary elements (e.g., a promoter, etc.) for enabling the expression of the antisense polynucleotide of the present invention, or can be produced by a known technique (e.g., Sambrook and Russell, Molecular Cloning A Laboratory Manual ($4^{th}$ Ed., 2001), Cold Spring Harbor Laboratory Press, JP Patent Publication (Kokai) No. 2016-153403 A, JP Patent Publication (Kokai) No. 2016-025853 A). The cell, into which the antisense polynucleotide of the present invention has been introduced by such a method, can express the antisense polynucleotide of the present invention at a high level. Thus, such a cell is transplanted into cancer tissues, so that it can be utilized as a cell therapeutic agent for suppressing the growth of cancer.

<Type of Cancer>

The terms "tumor" and "cancer" are used in the present invention to mean malignant neoplasms, and are used interchangeably. The cancer to be targeted is not particularly limited. Specific examples include cancers developed in the bladder, bone, bone marrow, brain, breast, colon/rectum, esophagus, digestive tract, gum, head, kidney, liver, lung, nasopharynx, neck, ovary, prostate, skin, stomach, testicle, tongue, blood or uterus, and cancer and cancer cells derived from these organs. Preferred examples include colorectal cancer, breast cancer, lung cancer, liver cancer, pancreatic cancer, blood cancer, kidney cancer, brain tumors, stomach cancer, cervical cancer, uterine cancer, ovarian cancer, prostate cancer, bladder cancer, esophagus cancer, fibrosarcomas, mast cell tumors, and melanomas. Examples of these specific cancers include, but not limited thereto, mammary gland cancer, complex mammary gland cancer, mammary gland malignant mixed tumors, intraductal papillary adenocarcinomas, lung adenocarcinomas, squamous cell carcinomas, small cell carcinomas, large cell carcinomas, glioma which is a neuroepithelial tissue tumor, ependymomas, neurocytomas, embryonal neuroectodermal tumors, schwannomas, neurofibromas, meningiomas, chronic lymphocytic leukemia, lymphomas, GI lymphomas, digestive lymphomas, small to medium cell lymphomas, cecal cancer, ascending colon cancer, descending colon cancer, transverse colon cancer, sigmoid colon cancer, rectal cancer, epithelial ovarian cancer, germ cell tumors, stromal cell tumors, pancreatic ductal cancer, invasive pancreatic ductal cancer, adenocarcinomas of pancreatic cancer, acinic cell carcinomas, adenosquamous carcinomas, giant cell tumors, intraductal papillary mucinous neoplasms, mucinous cystadenocarcinomas, pancreatoblastomas, serous cystadenocarcinomas, solid papillary cancer, gastrinomas, glucagonomas, insulinomas, multiple endocrine adenomatoses, non-functional islet cell tumors, somatostatinomas, and VlPomas.

Moreover, preferred examples of the subject to be targeted in the present invention include mammals, including primates such as human, livestock such as cow, pig, sheep and horse, companion animals such as dog and cat, and mammals kept in a zoo. Among others, human is preferable. In the present invention, the antisense polynucleotide of the present invention, or the pharmaceutical composition for treating and/or preventing cancer of the present invention, can be administered to a subject to treat and/or prevent cancer.

<Type of Antitumor Agent>

In the present invention, a drug formed by combining a pharmaceutical composition for treating and/or preventing cancer comprising, as an active ingredient, the above-described antisense polynucleotide, with another (typically, known) antitumor agent, or with a pharmaceutical composition comprising such an antitumor agent (referred to as a "combination drug") can be administered to a subject in combination, and thereby, the antitumor effects can be more preferably increased. The pharmaceutical composition for treating and/or preventing cancer of the present invention and another antitumor agent (or a pharmaceutical composition comprising another antitumor agent) can be administered to a subject, simultaneously or separately. In the case of the separate administration, either the pharmaceutical composition or the antitumor agent may be administered first or after, and the dose interval, the dose, the administration route and the number of doses can be suitably selected by a medical specialist. The dosage form of such another drug to be simultaneously administered with the pharmaceutical composition is, for example, a pharmaceutical compositions formulated by mixing the pharmaceutical composition for treating and/or preventing cancer of the present invention with the antitumor agent in a pharmaceutically acceptable carrier (or medium) (which is also referred to as a "mixed drug").

Examples of the antitumor agents include the following antitumor agents known in publications and the like.

Examples of alkylating agents such as Thiotepa and cyclophosphamide include: alkyl sulfonates like (i.e., "such as") Busulfan, improsulfan, and piposulfan; aziridines such as benzodopa, carboquone, meturedopa, and uredopa; ethyleneimines such as Altretamine, triethyleneamine, triethylenephosphoramide, triethilenethiophosphoramide, and trimethylolamine; acetogenins such as bullatacin and bullatacinone; camptothecin; bryostatin; callystatin; cryptophycin 1, and cryptophycin 8; dolastatin; duocarmycin; eleutherobin; pancratistatin; sarcodictyin; spongistatin; Nitrogen mustards such as chlorambucil, chlornaphazine, cholophosphamide, and estramustine; ifosfamide, mechlorethamine, mechlorethamine hydrochloride oxide, melphalan, temozolomide, novembichin; fenesterin, prednimustine, trofosfamide, uracil mustard; and nitrosoureas such as bendamustine, carmustine, chlorozotocin, streptozocin, fotemustine, lomustine, nimustine, and ranimnustine.

Examples of anticancer antibiotics include calicheamicin, dynemicin, clodronate, esperamicin, aclacinomycin, actinomycin, authramycin, azaserine, bleomycin, cactinomycin, carabicin, carminomycin, carzinophilin, chromomycin, dactinomycin, daunorubicin, detorubicin, 6-diazo-5-oxo-L-norleucine, adriamycin (doxorubicin), bleomycin, aclarbicin, amrubicin, epirubicin, esorubicin, idarubicin, marcellomycin, mitomycin C, mycophenolic acid, nogalamycin, olivomycin, peplomycin, potfiromycin, puromycin, quelamycin, rodorubicin, streptonigrin, streptozocin, tubercidin, ubenimex, zinostatin, and zorubicin.

Examples of antimetabolites include: folic acid analogs such as denopterin, pteropterin, methotrexate, trimetrexate, and pemetrexed; purine analogs such as fludarabine, 6-mercaptopurine, thiamiprine, thioguanine, cladribine, and clofarabine; pyrimidine analogs such as ancitabine, azacitidine, 6-azauridine, carmofur, cytarabine, dideoxyuridine, doxifluridine, enocitabine, floxuridine, trifluridine, capecitabine, 5-FU, gemcitabine, S-1, and tegafur; and hydroxycarbamide and nelarabine.

Examples of hormone preparations include anastrozole, bicalutamide, degarelix, estramustine, exemestane, flutamide, fulvestrant, goserelin, letrozole, leuplin, medroxyprogesterone, mepitiostane, octreotide, tamoxifen, and toremifene. Specific examples include: androgen preparations such as calusterone, drostanolone propionate, epitiostanol, mepitiostane, testolactone, and enzalutamide; antiadrenal preparations such as aminoglutethimid, mitotane, and trilostane; and frolinic acid, aceglatone, aldophosphamide glycoside, aminolevulinic acid, eniluracil, amsacrine, bestrabucil, bisantrene, edatraxate, defofamine, demecolcine, diaziquone, elformithine, elliptinium acetate, epothilone, etoglucid, lenthinan, lonidamine, maytansine, ansamitocine, abiraterone, mitoguazone, mitoxantrone, mopidanmol, nitraerine, pentostatin, phenamet, pirarubicin, losoxantrone, podophyllin acid, 2-ethyl hydrazide, procarbazine, razoxane, rhizoxin, sizofiran, spirogermanium, tenuazonic acid, triaziquone, Roridin A, anguidine, urethane, vindesine, dacarbazine, mannomustine, mitobronitol, mitolactol, pipobroman, gacytosine, arabinoside, BCG, Krestin, and picibanil.

Examples of other anticancer agents such as those derived from plants include docetaxel, etoposide, teniposide, irinotecan, nogitecan, paclitaxel, cabazitaxel, vinblastine, vincristine, vindesine, vinorelbine, carboplatin, cisplatin, dacarbazine, eribulin, L-asparaginase, miriplatin, mitoxantrone, nedaplatin, oxaliplatin, pentostatin, procarbazine, arsenic trioxide, sobuzoxane, tamibarotene, mitoxantrone, novantrone, edatrexate, ibandronate, topoisomerase inhibitor, difluoromethylornithine (DMFO), and retinoic acid.

Examples of molecular target drugs include afatinib, axitinib, alectinib, bevacizumab, cetuximab, crizotinib, erlotinib, everolimus, gefitinib, lapatinib, ramucirumab, panitumumab, pazopanib, pertuzumab, nivolumab, regorafenib, lenvatinib, sorafenib, sunitinib, temsirolimus, trastuzumab, and pharmaceutically acceptable salts or derivatives thereof.

Further, radioisotopes such as $^{211}$At, $^{131}$I, $^{125}$I, $^{90}$Y, $^{186}$Re, $^{188}$Re, $^{153}$SM, $^{212}$Bi, $^{32}$P, $^{175}$Lu, and $^{176}$Lu, which are known in publications and the like, may also be used as antitumor agents. Radioisotopes are desirably those effective for treating and diagnosing tumors, and such radioisotopes may also be included in the pharmaceutical composition for treating and/or preventing cancer of the present invention.

<Treatment and Prevention Methods>

Further, the present invention also provides a method for treating and/or preventing cancer in a subject, wherein the method comprises administering the pharmaceutical composition for treating and/or preventing cancer of the present invention, or a combination drug comprising the pharmaceutical composition for treating and/or preventing cancer of the present invention and the above-described another antitumor agent (or a pharmaceutical composition comprising such an antitumor agent), to a subject who suffers (or has suffered) from cancer.

The terms "treatment of cancer" and "antitumor effects" are used in the present description to mean the effects of the antisense polynucleotide of the present invention or the pharmaceutical composition for treating and/or preventing cancer of the present invention on cancer cells and tumors, which are compared with a negative control which is not treated with the antisense polynucleotide of the present invention or the pharmaceutical composition for treating and/or preventing cancer of the present invention. Thus, examples of the matters indicated by these terms not only include complete inhibition of the growth of cancer cells and regression or disappearance of tumors, but also include retardation of the growth of cancer cells in comparison to the negative control that is not treated with the antisense polynucleotide of the present invention or the pharmaceutical composition for treating and/or preventing cancer of the present invention (i.e., a reduction in the amount of cancer cells increased) and retardation of tumor growth.

The term "prevention" is used in the present description to include prevention of cancer recurrence for reducing the risk of recurrence after completion of cancer treatments by a cancer therapy such as surgery, chemotherapy, radiotherapy, or immunotherapy.

For the above-described pharmaceutical composition, combination drug, antisense polynucleotide used as active ingredient, dosage, usage, preparation form, and the type of cancer to be targeted, the same contents as described above also apply into this section.

EXAMPLES

The present invention will be more specifically described in the following examples. However, these examples are not intended to limit the scope of the present invention.

Example 1

Effectiveness of Antisense RNA of hsa-miR4454 on Pancreatic Cancer Cells

Figure 2:
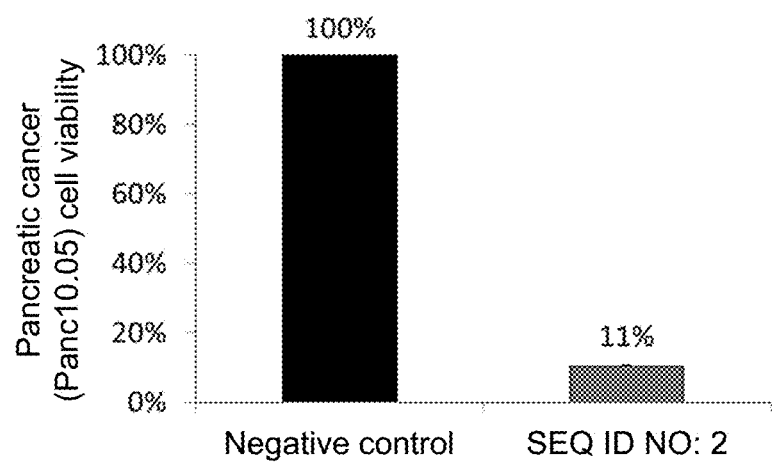
FIG. 2 shows the ratio (cell viability) of the viable cell count of the pancreatic cancer cell line Panc 10.05, into which the antisense RNA (SEQ ID NO: 2) of hsa-miR4454 as set forth in SEQ ID NO: 1 has been introduced, to the viable cell count (100%) of the pancreatic cancer cell line Panc 10.05, into which the synthetic RNA of a negative control oligo has been introduced.

A synthetic RNA having the nucleotide sequence as set forth in SEQ ID NO: 2 that is the antisense RNA of hsa-miR4454 (hereinafter referred to as "antisense RNA") was evaluated in terms of effectiveness on pancreatic cancer cells. A Panc-1 cell line (ATCC® CRL-1469™) used as pancreatic cancer cells was seeded in a DMEM medium (Nacalai Tesque, Japan) supplemented with 10% FBS, and also, a Panc 10.05 cell line (ATCC®CRL-2547™) used as pancreatic cancer cells was seeded in an RPMI medium (Nacalai Tesque, Japan) supplemented with 10% FBS, and thereafter, individual cell lines were cultured under conditions of 37° C. and 5% $CO_2$. Specifically, $6×10^3$ cells were seeded per well of a 96-well plate, and thereafter, antisense RNA (Thermo Fisher Scientific Inc. mirVana™ miRNA Inhibitors) or negative control oligo (Thermo Fisher Scientific Inc. mirVana™ miRNA Inhibitor, Negative Control) in a concentration of 30 nM, respectively, was introduced into the pancreatic cancer cells, using Lipofectamine RNAiMAX (Thermo Fisher Scientific Inc.). Twenty-four hours after the gene introduction, the culture medium was replaced with a fresh one, and the number of cells was counted for 5 days for each of the pancreatic cancer cells into which the negative control oligo had been introduced (negative control cells) and the pancreatic cancer cells into which the antisense RNA had been introduced (antisense RNA-introduced cells). The number of cells was measured by measuring the ATP activity using a Celtiter-glo (Promega Corporation) reagent, and the obtained measurement value was used as an indicator of the viable cell count. The measurement was carried out at n=3, and the ratio of the viable cell count of the pancreatic cancer cells, into which the antisense RNA had been introduced, to the viable cell count (100%) of the negative control cells, is defined to be the viability (%) of pancreatic cancer cells, and the results are shown as mean±standard deviation. The evaluation results are shown in FIG. 1 and FIG. 2. As shown in FIG. 1, the Panc-1 cell line, into which the antisense RNA had been introduced, was found to have cell viability of 68%, in comparison to the Panc-1 cell line, into which the negative control oligo had been introduced. In addition, as shown in FIG. 2, the Panc 10.05 cell line, into which the antisense RNA had been introduced, was found to have cell viability of 11%, in comparison to the Panc 10.05 cell line, into which the negative control oligo had been introduced.

Example 2

Effectiveness of Antisense RNA of hsa-miR4454 on Breast Cancer Cell

Figure 3:
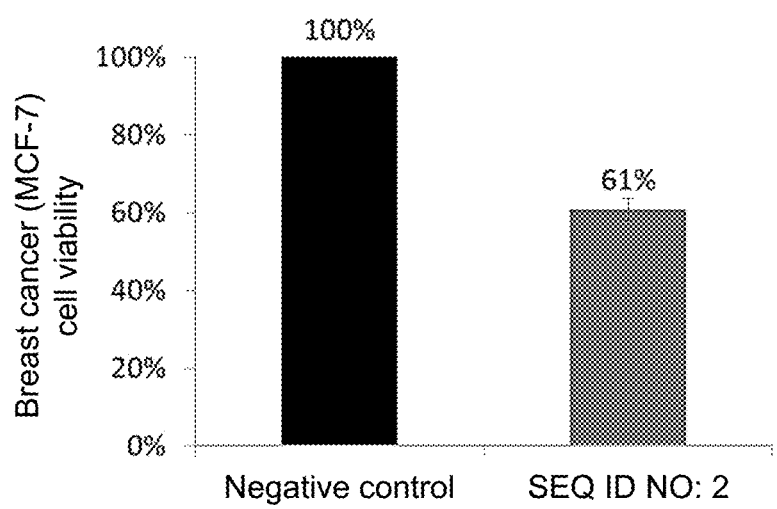
FIG. 3 shows the ratio (cell viability) of the viable cell count of the breast cancer cell line MCF-7, into which the antisense RNA (SEQ ID NO: 2) of hsa-miR4454 as set forth in SEQ ID NO: 1 has been introduced, to the viable cell count (100%) of the breast cancer cell line MCF-7, into which the synthetic RNA of a negative control oligo has been introduced.

The effectiveness of the antisense RNA of Example 1 on breast cancer cells was evaluated. An MCF-7 cell line (ATCC® HTB-22™) used as breast cancer cells was seeded in an RPMI medium (Nacalai Tesque, Japan) supplemented with 10% FBS, and thereafter, the cell line was cultured under conditions of 37° C. and 5% $CO_2$. Specifically, $6×10^3$ cells were seeded per well of a 96-well plate, and thereafter, antisense RNA (Thermo Fisher Scientific Inc. mirVana™ miRNA Inhibitors) or negative control oligo (Thermo Fisher Scientific Inc. mirVana™ miRNA Inhibitor, Negative Control) in a concentration of 30 nM, respectively, was introduced into the breast cancer cells, using Lipofectamine RNAiMAX (Thermo Fisher Scientific Inc.). Twenty-four hours after the gene introduction, the culture medium was replaced with a fresh one, and the number of cells was counted for 5 days for each of the breast cancer cells into which the negative control oligo had been introduced (negative control cells) and the breast cancer cells into which the antisense RNA had been introduced (antisense RNA-introduced cells). The number of cells was measured by measuring the ATP activity using a Celtiter-glo (Promega Corporation) reagent, and the obtained measurement value was used as an indicator of the viable cell count. The measurement was carried out at n=3, and the ratio of the viable cell count of the breast cancer cells, into which the antisense RNA had been introduced, to the viable cell count (100%) of the negative control cells, is defined to be the viability (%) of breast cancer cells, and the results are shown as mean±standard deviation. The evaluation results are shown in FIG. 3. As shown in FIG. 3, the breast cancer cells, into which the antisense RNA had been introduced, was found to have cell viability of 61%, in comparison to the breast cancer cells, into which the negative control oligo had been introduced.

Example 3

Effectiveness of Antisense RNA of hsa-miR4454 on Lung Cancer Cells

Figure 4:
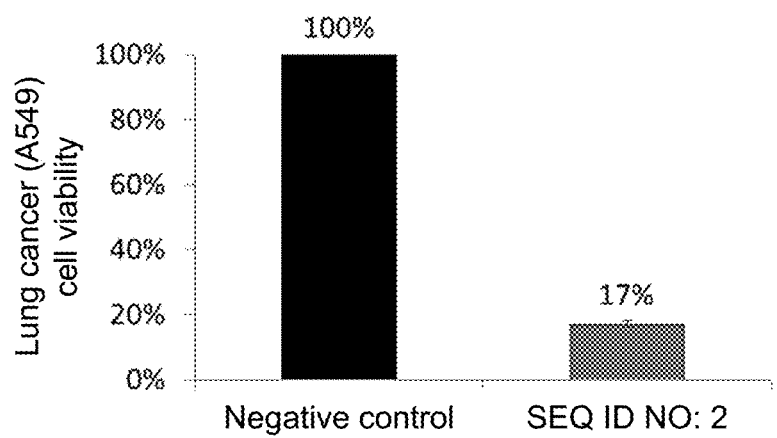
FIG. 4 shows the ratio (cell viability) of the viable cell count of the lung cancer cell line A549, into which the antisense RNA (SEQ ID NO: 2) of hsa-miR4454 as set forth in SEQ ID NO: 1 has been introduced, to the viable cell count (100%) of the lung cancer cell line A549, into which the synthetic RNA of a negative control oligo has been introduced.

The effectiveness of the antisense RNA of Example 1 on lung cancer cells was evaluated. An A549 cell line (ATCC® CCL-185™) used as lung cancer cells was seeded in an RPMI medium (Nacalai Tesque, Japan) supplemented with 10% FBS, and thereafter, the cell line was cultured under conditions of 37° C. and 5% $CO_2$. Specifically, $2×10^3$ cells were seeded per well of a 96-well plate, and thereafter, antisense RNA (Thermo Fisher Scientific Inc. mirVana™ miRNA Inhibitors) or negative control oligo (Thermo Fisher Scientific Inc. mirVana™ miRNA Inhibitor, Negative Control) in a concentration of 30 nM, respectively, was introduced into the lung cancer cells, using Lipofectamine RNAiMAX (Thermo Fisher Scientific Inc.). Twenty-four hours after the gene introduction, the culture medium was replaced with a fresh one, and the number of cells was counted for 5 days for each of the lung cancer cells into which the negative control oligo had been introduced (negative control cells) and the lung cancer cells into which the antisense RNA had been introduced (antisense RNA-introduced cells). The number of cells was measured by measuring the ATP activity using a Celtiter-glo (Promega Corporation) reagent, and the obtained measurement value was used as an indicator of the viable cell count. The measurement was carried out at n=3, and the ratio of the viable cell count of the lung cancer cells, into which the antisense RNA had been introduced, to the viable cell count (100%) of the negative control cells, is defined to be the viability (%) of lung cancer cells, and the results are shown as mean±standard deviation. The evaluation results are shown in FIG. 4. As shown in FIG. 4, the lung cancer cells, into which the antisense RNA had been introduced, was found to have cell viability of 17%, in comparison to the lung cancer cells, into which the negative control oligo had been introduced.

Example 4

Effectiveness of Antisense RNA of hsa-miR4454 on Liver Cancer Cells

Figure 5:
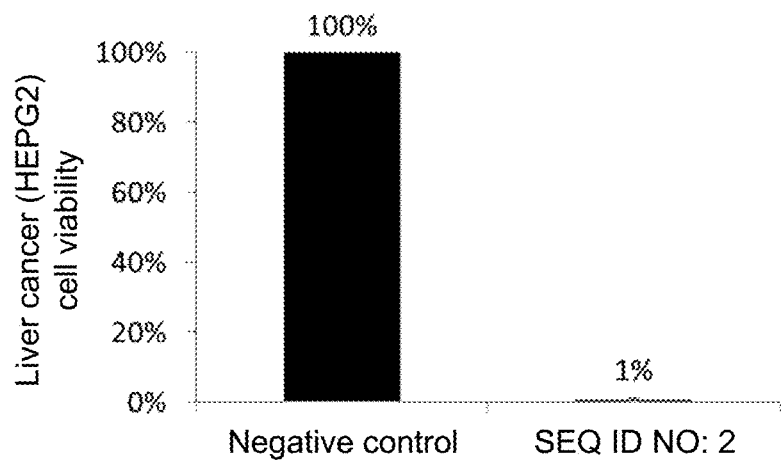
FIG. 5 shows the ratio (cell viability) of the viable cell count of the liver cancer cell line HEPG2, into which the antisense RNA (SEQ ID NO: 2) of hsa-miR4454 as set forth in SEQ ID NO: 1 has been introduced, to the viable cell count (100%) of the liver cancer cell line HEPG2, into which the synthetic RNA of a negative control oligo has been introduced.

The effectiveness of the antisense RNA of Example 1 on liver cancer cells was evaluated. An HEPG2 cell line (ATCC® HB-8065™) used as liver cancer cells was seeded in an RPMI medium (Nacalai Tesque, Japan) supplemented with 10% FBS, and thereafter, the cell line was cultured under conditions of 37° C. and 5% $CO_2$. Specifically, $6×10^3$ cells were seeded per well of a 96-well plate, and thereafter, antisense RNA (Thermo Fisher Scientific Inc. mirVana™ miRNA Inhibitors) or negative control oligo (Thermo Fisher Scientific Inc. mirVana™ miRNA Inhibitor, Negative Control) in a concentration of 30 nM, respectively, was introduced into the liver cancer cells, using Lipofectamine RNAiMAX (Thermo Fisher Scientific Inc.). Twenty-four hours after the gene introduction, the culture medium was replaced with a fresh one, and the number of cells was counted for 5 days for each of the liver cancer cells into which the negative control oligo had been introduced (negative control cells) and the liver cancer cells into which the antisense RNA had been introduced (antisense RNA-introduced cells). The number of cells was measured by measuring the ATP activity using a Celtiter-glo (Promega Corporation) reagent, and the obtained measurement value was used as an indicator of the viable cell count. The measurement was carried out at n=3, and the ratio of the viable cell count of the liver cancer cells, into which the antisense RNA had been introduced, to the viable cell count (100%) of the negative control cells, is defined to be the viability (%) of liver cancer cells, and the results are shown as mean±standard deviation. The evaluation results are shown in FIG. 5. As shown in FIG. 5, the liver cancer cells, into which the antisense RNA had been introduced, was found to have cell viability of 1%, in comparison to the liver cancer cells, into which the negative control oligo had been introduced.

Example 5

Effectiveness of Antisense RNA of hsa-miR4454 on Blood Cancer Cells

Figure 6:
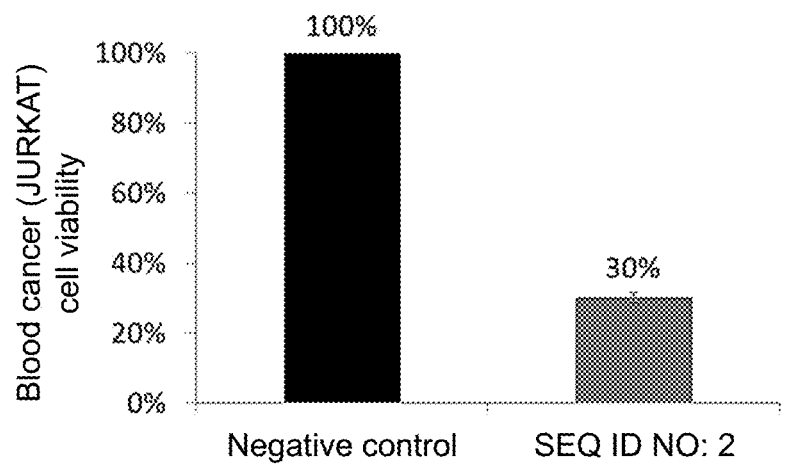
FIG. 6 shows the ratio (cell viability) of the viable cell count of the blood cancer cell line JURKAT, into which the antisense RNA (SEQ ID NO: 2) of hsa-miR4454 as set forth in SEQ ID NO: 1 has been introduced, to the viable cell count (100%) of the blood cancer cell line JURKAT, into which the synthetic RNA of a negative control oligo has been introduced.

The effectiveness of the antisense RNA of Example 1 on blood cancer cells was evaluated. A JURKAT cell line (ATCC® TIB-152™) used as blood cancer cells was seeded in an RPMI medium (Nacalai Tesque, Japan) supplemented with 10% FBS, and thereafter, the cell line was cultured under conditions of 37° C. and 5% $CO_2$. Specifically, $4×10^4$ cells were seeded per well of a 96-well plate, and thereafter, antisense RNA (Thermo Fisher Scientific Inc. mirVana™ miRNA Inhibitors) or negative control oligo (Thermo Fisher Scientific Inc. mirVana™ miRNA Inhibitor, Negative Control) in a concentration of 30 nM, respectively, was introduced into the blood cancer cells, using Viromer (Lipocalyx). The number of cells was counted for 5 days for each of the blood cancer cells into which the negative control oligo had been introduced (negative control cells) and the blood cancer cells into which the antisense RNA had been introduced (antisense RNA-introduced cells). The number of cells was measured by measuring the ATP activity using a Celtiter-glo (Promega Corporation) reagent, and the obtained measurement value was used as an indicator of the viable cell count. The measurement was carried out at n=3, and the ratio of the viable cell count of the blood cancer cells, into which the antisense RNA had been introduced, to the viable cell count (100%) of the negative control cells, is defined to be the viability (%) of blood cancer cells, and the results are shown as mean±standard deviation. The evaluation results are shown in FIG. 6. As shown in FIG. 6, the blood cancer cells, into which the antisense RNA had been introduced, was found to have cell viability of 30%, in comparison to the blood cancer cells, into which the negative control oligo had been introduced.

Example 6

Effectiveness of Antisense RNA of hsa-miR4454 on Colorectal Cancer Cells

Figure 7:
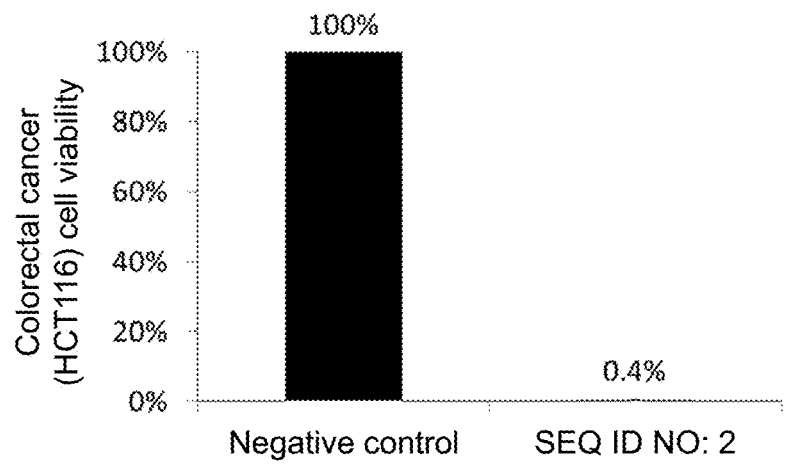
FIG. 7 shows the ratio (cell viability) of the viable cell count of the colorectal cancer cell line HCT116, into which the antisense RNA (SEQ ID NO: 2) of hsa-miR4454 as set forth in SEQ ID NO: 1 has been introduced, to the viable cell count (100%) of the colorectal cancer cell line HCT116, into which the synthetic RNA of a negative control oligo has been introduced.

The effectiveness of the antisense RNA of Example 1 on colorectal cancer cells was evaluated. An HCT116 cell line (ATCC® CCL-247™) used as colorectal cancer cells was seeded in a McCoy's medium (Nacalai Tesque, Japan) supplemented with 10% FBS, and thereafter, the cell line was cultured under conditions of 37° C. and 5% $CO_2$. Specifically, $6×10^3$ cells were seeded per well of a 96-well plate, and thereafter, antisense RNA (Thermo Fisher Scientific Inc. mirVana™ miRNA Inhibitors) or negative control oligo (Thermo Fisher Scientific Inc. mirVana™ miRNA Inhibitor, Negative Control) in a concentration of 30 nM, respectively, was introduced into the colorectal cancer cells, using Lipofectamine RNAiMAX (Thermo Fisher Scientific Inc.). Twenty-four hours after the gene introduction, the culture medium was replaced with a fresh one, and the number of cells was counted for 5 days for each of the colorectal cancer cells into which the negative control oligo had been introduced (negative control cells) and the colorectal cancer cells into which the antisense RNA had been introduced (antisense RNA-introduced cells). The number of cells was measured by measuring the ATP activity using a Celtiter-glo (Promega Corporation) reagent, and the obtained measurement value was used as an indicator of the viable cell count. The measurement was carried out at n=3, and the ratio of the viable cell count of the colorectal cancer cells, into which the antisense RNA had been introduced, to the viable cell count (100%) of the negative control cells, is defined to be the viability (%) of colorectal cancer cells, and the results are shown as mean±standard deviation. The evaluation results are shown in FIG. 7. As shown in FIG. 7, the colorectal cancer cells, into which the antisense RNA had been introduced, was found to have cell viability of 0.4%, in comparison to the colorectal cancer cells, into which the negative control oligo had been introduced.

Comparative Example 1

Effectiveness of Synthetic RNA of hsa-miR4454 on Colorectal Cancer Cells

Figure 8:
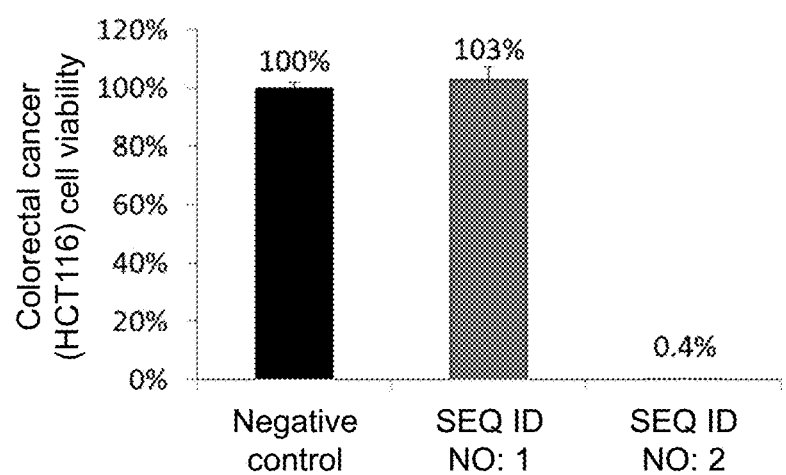
FIG. 8 shows the ratios (cell viability) of the viable cell count of the colorectal cancer cell line HCT116, into which the antisense RNA (SEQ ID NO: 2) of hsa-miR4454 as set forth in SEQ ID NO: 1 and synthetic RNA having the same nucleotide sequence as hsa-miR4454 as set forth in SEQ ID NO: 1 have been introduced, to the viable cell count (100%) of the colorectal cancer cell line HCT116, into which the synthetic RNA of a negative control oligo has been introduced.

The effectiveness of synthetic RNA having the same nucleotide sequence as hsa-miR4454 as set forth in SEQ ID NO: 1 (Thermo Fisher Scientific Inc. mirVana™ miRNA Mimics) on colorectal cancer was evaluated in accordance with the method described in Example 6. The evaluation results are shown in FIG. 8. As shown in FIG. 8, the cell viability of the colorectal cancer cells, into which the antisense RNA of hsa-miR4454 had been introduced, was 0.4%, whereas the cell viability of the colorectal cancer cells, into which the synthetic RNA having the nucleotide sequence as set forth in SEQ ID NO: 1 had been introduced, was 103%.

Comparative Example 2

Effectiveness of Antisense RNAs of miRNAs Known as Cancer Markers

Figure 9:
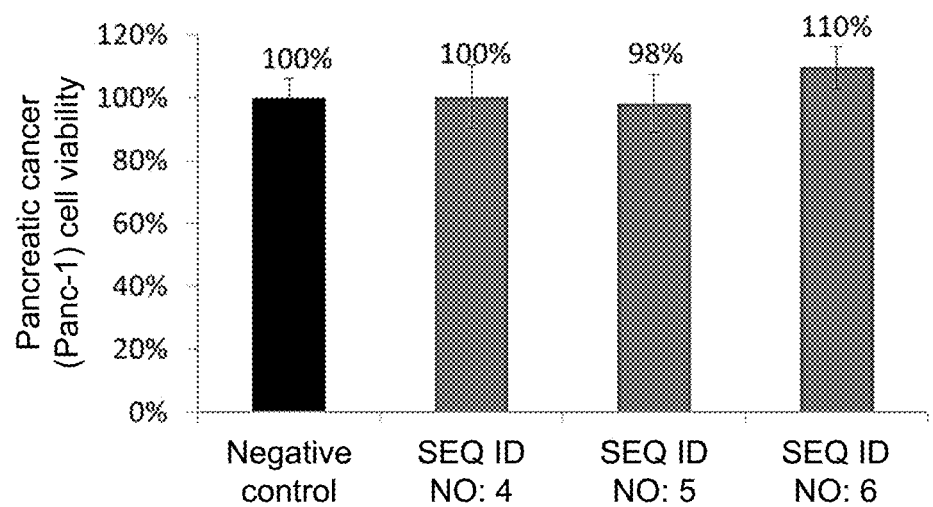
FIG. 9 shows the ratio (cell viability) of the viable cell count of the pancreatic cancer cell line Panc-1, into which the antisense RNA of hsa-miR4294 as set forth in SEQ ID NO: 4, hsa-miR6799-5p as set forth in SEQ ID NO: 5, or hsa-miR125a-3p as set forth in SEQ ID NO: 6 has been introduced, to the viable cell count (100%) of the pancreatic cancer cell line Panc-1, into which the synthetic RNA of a negative control oligo has been introduced.
Figure 10:
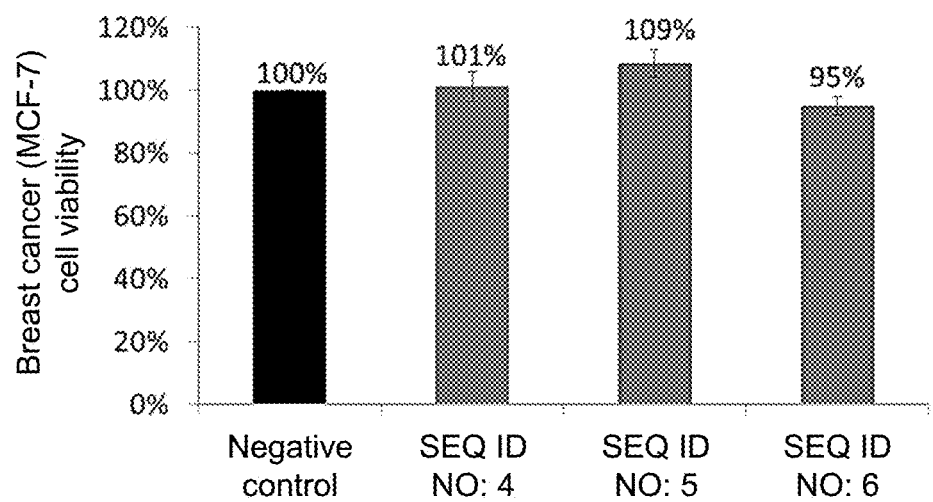
FIG. 10 shows the ratio (cell viability) of the viable cell count of the breast cancer cell line MCF-7, into which the antisense RNA of hsa-miR4294 as set forth in SEQ ID NO: 4, hsa-miR6799-5p as set forth in SEQ ID NO: 5, or hsa-miR125a-3p as set forth in SEQ ID NO: 6 has been introduced, to the viable cell count (100%) of the breast cancer cell line MCF-7, into which the synthetic RNA of a negative control oligo has been introduced.
Figure 11:
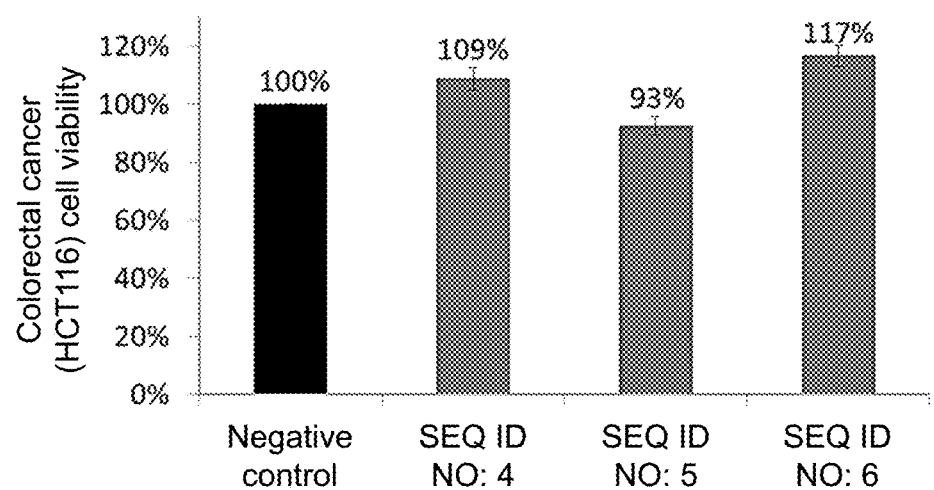
FIG. 11 shows the ratio (cell viability) of the viable cell count of the colorectal cancer cell line HCT116, into which the antisense RNA of hsa-miR4294 as set forth in SEQ ID NO: 4, hsa-miR6799-5p as set forth in SEQ ID NO: 5, or hsa-miR125a-3p as set forth in SEQ ID NO: 6 has been introduced, to the viable cell count (100%) of the colorectal cancer cell line HCT116, into which the synthetic RNA of a negative control oligo has been introduced.

The effectiveness of the antisense RNA (Thermo Fisher Scientific Inc. mirVana™ miRNA Inhibitors) of hsa-miR4294 as set forth in SEQ ID NO: 4 (miRBase Accession No.MIMAT0016849), hsa-miR6799-5p as set forth in SEQ ID NO: 5 (miRBase Accession No.MIMAT0027498), or hsa-miR125a-3p as set forth in SEQ ID NO: 6 (miRBase Accession No.MIMAT0004602) (Kojima M PLoS One. 10(2) (2015) "MicroRNA markers for the diagnosis of pancreatic and biliary-tract cancers.") (see Table 2 for the nucleotide sequences as set forth in SEQ ID NOs: 4, 5 and 6), all of which have been known as pancreatic cancer markers, as with hsa-miR4454, on pancreatic cancer cells, breast cancer cells, and colorectal cancer cells, was evaluated in accordance with the methods described in Examples 1, 2, and 6, respectively. The evaluation results are shown in FIGS. 9, 10, and 11, respectively. The cell viabilities of the pancreatic cancer cells, into which the antisense RNAs of hsa-miR4294, hsa-miR6799-5p and hsa-miR125a-3p had been each introduced, were 100%, 98%, and 110%, respectively (FIG. 9). The cell viabilities of the breast cancer cells were 101%, 109%, and 95%, respectively (FIG. 10). The cell viabilities of the colorectal cancer cells were 109%, 93%, and 117%, respectively (FIG. 11). All of the antisense RNAs did not have antitumor effects.

TABLE 2

| SEQ ID NO. | Nucleotide sequence | Gene name miRBase Accession No. |
|---|---|---|
| 4 | GGGAGUCUACAGCAGGG | hsa-miR-4294 (MIMAT0016849) |
| 5 | GGGGAGGUGUGCAGGGCUGG | hsa-miR-6799-5p (MIMAT0027498) |
| 6 | ACAGGUGAGGUUCUUGGGAGCC | hsa-miR-125a-3p (MIMAT0004602) |

Example 7

Figure 12A:
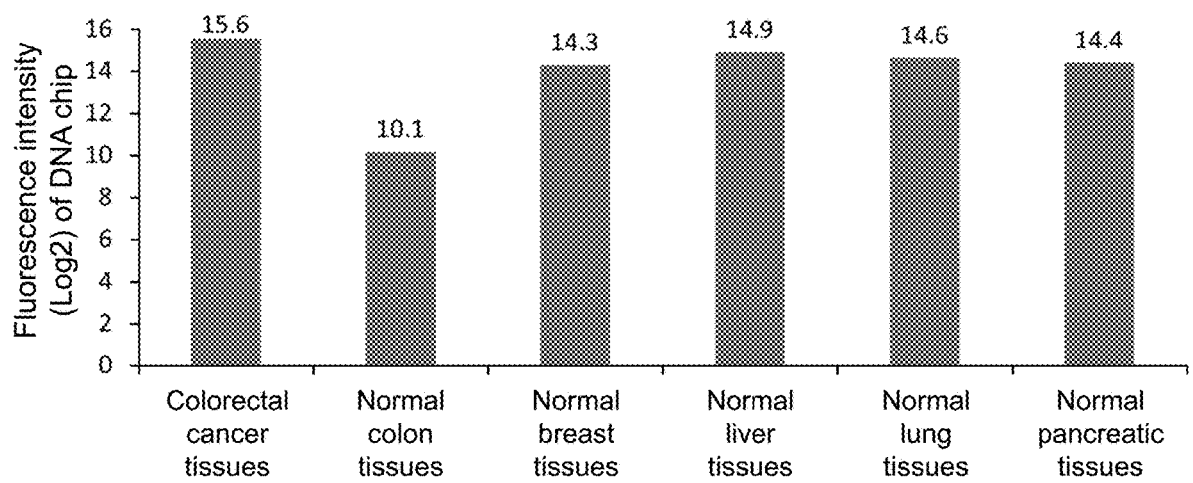
FIG. 12A shows the signal expression level of hsa-miR4454 as set forth in SEQ ID NO: 1 in the DNA chips of colorectal cancer tissues, normal colon tissues, normal breast tissues, normal liver tissues, normal lung tissues, and normal pancreatic tissues.
Figure 12B:
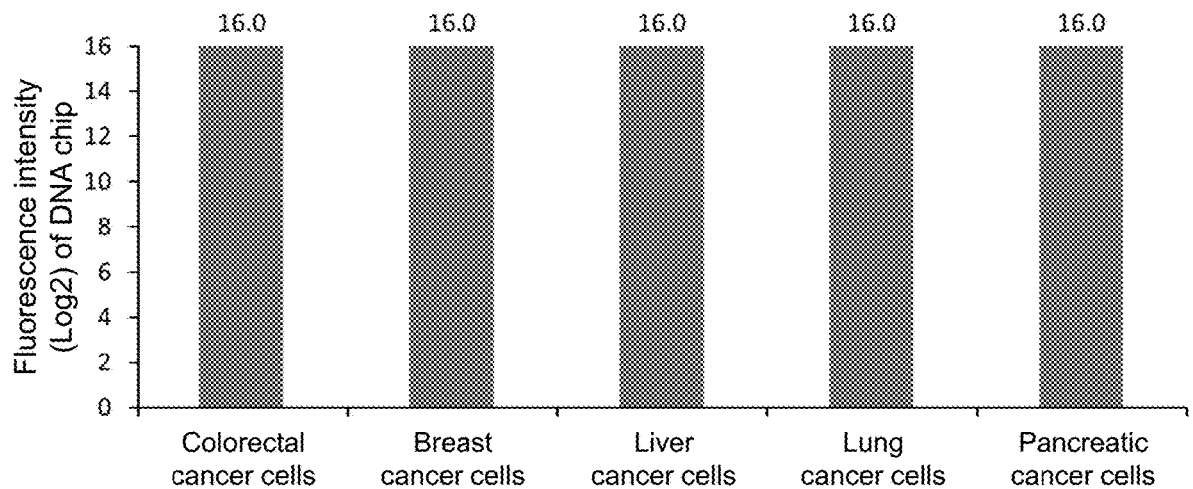
FIG. 12B shows the signal expression level of hsa-miR4454 as set forth in SEQ ID NO: 1 in the DNA chips of colorectal cancer cells, breast cancer cells, liver cancer cells, lung cancer cells, and pancreatic cancer cells.

Expression Level of hsa-miR4454 in Cancer Tissues, Cancer Cells, and Normal Tissues <Extraction of Total RNA>
Total RNAs (Thermo Fisher Scientific Inc.), which were derived from colorectal cancer tissues, normal colon tissues, normal breast tissues, normal lung tissues, normal liver tissues, and normal pancreatic tissues, were used as total RNAs derived from various tissues. In addition, as total RNAs derived from cells, total RNAs were obtained from colorectal cancer cells, breast cancer cells, lung cancer cells, liver cancer cells, and pancreatic cancer cells ($10^7$ cells each), using miRNeasyminikit (Qiagen), in accordance with the protocols determined by the manufacturer.
<Measurement of Expression Level of Gene>
With respect to the above-described total RNAs, miRNA was fluorescently labeled using a 3D-Gene (registered trademark) miRNA Labeling kit (TORAY INDUSTRIES, INC.), in accordance with the protocols determined by the manufacturer. A 3D-Gene (registered trademark) Human miRNA Oligo chip (TORAY INDUSTRIES, INC.), which includes probes having sequences complementary to 2,565 types of miRNAs, among the miRNAs registered in miRBase release 21, was used as an oligo DNA chip, and hybridization and washing after the hybridization were carried out under stringent conditions in accordance with the protocols determined by the manufacturer. The DNA chip was scanned using a 3D-Gene (registered trademark) scanner (TORAY INDUSTRIES, INC.) to obtain an image, and then, fluorescence intensity was quantified. The quantified fluorescence intensity was converted to a logarithm, the base of which was 2, and the obtained value was defined as a gene expression level. Subtraction of a blank value was carried out, and a missing value was replaced with a signal value of 0.1. As a result, the comprehensive gene expression levels of miRNAs with respect to the above-described cells and tissues were obtained. The results of tissues (cancer, normal) are shown in FIG. 12A, and the results of cells (cancer) are shown in FIG. 12B. From these results, it was demonstrated that hsa-miR4454 as set forth in SEQ ID NO: 1 is expressed in various types of cancer cells, cancer tissues and normal tissues, and that the expression level of hsa-miR4454 in cancer tissues and cancer cells is higher than the expression level of hsa-miR4454 in normal tissues.

INDUSTRIAL APPLICABILITY

The pharmaceutical composition for treating cancer of the present invention is useful in the treatment and/or prevention of cancer.

All publications, patents, and patent applications cited in the present description are incorporated herein by reference in their entirety.

The invention claimed is:

1. A method for treating cancer in a subject who suffers or has suffered from the cancer, comprising administering a pharmaceutical composition comprising, as an active ingredient and in an amount effective to treat the cancer, an antisense polynucleotide of microRNA hsa-miR-4454, wherein the cancer overexpresses hsa-miR-4454, and wherein the cancer is colorectal cancer, breast cancer, lung cancer, or pancreatic cancer.

2. The method according to claim 1, wherein the antisense polynucleotide is RNA or DNA.

3. The method according to claim 1, wherein the antisense polynucleotide comprises a nucleotide sequence having a sequence identity of 90% or more to a nucleotide sequence complementary to the nucleotide sequence as set forth in SEQ ID NO: 1.

4. The method according to claim 1, wherein the nucleotide sequence length of the antisense polynucleotide is 8 to 60 nucleotides.

5. The method according to claim 1, wherein the antisense polynucleotide consists of the nucleotide sequence as set forth in SEQ ID NO: 2 or 3.

6. The method according to claim 1, wherein the antisense polynucleotide is inserted into a vector, so that it can be expressed in the form of RNA or DNA.

7. The method according to claim 1, wherein the antisense polynucleotide is encapsulated into a carrier selected from the group consisting of non-cationic polymer carriers, liposome carriers, dendritic carriers, nano-material carriers, microparticle carriers, biostructural carriers, micelle carriers, polymer microparticles, and magnetic microparticles.

8. The method according to claim 1, wherein the pharmaceutical composition is administered in combination with an antitumor agent.

* * * * *